(12) United States Patent
Katsenelson et al.

(10) Patent No.: US 12,123,053 B2
(45) Date of Patent: Oct. 22, 2024

(54) MOLECULAR GLUE SCREENING ASSAYS AND METHODS FOR PRACTICING SAME

(71) Applicant: Eurofins DiscoverX Corporation, San Diego, CA (US)

(72) Inventors: Ksenya Cohen Katsenelson, La Jolla, CA (US); Daniel Kelly Treiber, San Diego, CA (US)

(73) Assignee: Eurofins DiscoverX Corporation, San Diego, CA (US)

( * ) Notice: Subject to any disclaimer, the term of this patent is extended or adjusted under 35 U.S.C. 154(b) by 0 days.

(21) Appl. No.: 17/584,315

(22) Filed: Jan. 25, 2022

(65) Prior Publication Data
US 2022/0243255 A1 Aug. 4, 2022

Related U.S. Application Data

(60) Provisional application No. 63/143,255, filed on Jan. 29, 2021.

(51) Int. Cl.
*C12Q 1/686* (2018.01)
*C12N 9/00* (2006.01)

(52) U.S. Cl.
CPC .............. *C12Q 1/686* (2013.01); *C12N 9/93* (2013.01)

(58) Field of Classification Search
CPC .......... C12Q 1/686; C12N 9/93; C12N 9/104; G01N 2500/02; G01N 33/5008; C07K 2319/95
See application file for complete search history.

(56) References Cited

U.S. PATENT DOCUMENTS 10,145,848 B2   12/2018   Crews et al.

FOREIGN PATENT DOCUMENTS

WO   WO2018-085247 A   5/2018

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Eurofins Discoverx Corporation, Application No. PCT/US2022/013770, Int'l filing date Jan. 25, 2022, International Preliminary Examination Report (IPER) mailed Aug. 10, 2023.
Simonetta, K. R. et al., 'Prospective discovery of small molecule enhancers of an E3 ligase-substrate interaction', Nature Communications, 2019, vol. 10, Article No. 1402, pp. 1-12.
Internet webpages, Katsenelson, K. C. et al., 'E3scanSM Ligand Binding Assay Platform for Targeted Protein Degradation and PROTAC® Discovery', Eurofins Discovery, 2020, http://www.chayon.co.kr/wp-content/uploads/2020/10/Eurofins-Discovery-E3scan-Poster-DDC2020-21153_081720.pdf.
Mayor-Ruiz, C. et al., 'Rational discovery of molecular glue degraders via scalable chemical profiling', nature chemical biology, 2020, vol. 16, pp. 1199-1207.
Eurofins Discoverx Corporation, Application No. PCT/US2022/013770, Int'l filing date Jan. 25, 2022, International Search Report dated May 11, 2022.
Eurofins Discoverx Corporation, Application No. PCT/US2022/013770, Int'l filing date Jan. 25, 2022, Written Opinion dated May 11, 2022.

* cited by examiner

*Primary Examiner* — Iqbal H Chowdhury
(74) *Attorney, Agent, or Firm* — Punita Bhasin

(57) ABSTRACT

The present disclosure provides a compound screening method comprising screening a test compound that binds a target protein of interest and another ligand protein that is not previously known to form a complex, comprising, (i) in the presence and absence of a test compound, incubating an immobilized ligand protein with a target protein of interest, comprising a nucleic acid tag, wherein the protein of interest and the nucleic acid tag differ from each other; (ii) removing unbound target protein of interest; and (iii) detecting the presence or absence of complex between the immobilized ligand protein, test compound, and the target protein of interest, wherein an increase in the amount of target protein of interest bound to the immobilized ligand protein in the presence of test compound as compared to the absence of test compound indicates the test compound binds to and enables protein-protein complex formation between the immobilized ligand protein and the target protein of interest.

19 Claims, 2 Drawing Sheets

US 12,123,053 B2

MOLECULAR GLUE SCREENING ASSAYS AND METHODS FOR PRACTICING SAME

PRIORITY CLAIM AND CROSS-REFERENCE TO RELATED APPLICATIONS

This application claims the benefit and priority of the U.S. provisional application No. 63/143,255, filed Jan. 29, 2021, the disclosure of which is incorporated by reference herein in its entirety, including all references and appendices cited therein, for all purposes.

FIELD OF INVENTION

The subject matter provided herein relates to screening compounds with properties of forming a protein-protein complex. More specifically, the subject matter provided herein relates to a screening assay to identify compounds capable of forming a protein-protein complex which, in some instances, might be targeted for degradation.

BACKGROUND

Protein degradation is a natural process in the body wherein proteins once tagged with a ubiquitin such as E3 ubiquitin ligase are routed for degradation via the cellular degradation machinery such as the proteasome. The process of protein degradation helps remove unwanted proteins (due to a biological reason) from the cell system and route such proteins to proteasomes, also known as the cell's trash compactor.

Targeted protein degradation, or TPD, uses small molecules to hijack the cellular degradation machinery by recruiting E3 ubiquitin ligases to proteins of interest (e.g. a protein identified in a diseased state) to induce their ubiquitin-dependent degradation. TPD is of interest in drug development, as it can address previously considered undruggable targets (80% of the human proteome) that cannot be inhibited with traditional small molecule inhibitors, such as scaffold proteins and transcription factors. It's been 20 years since the introduction of the first degrader molecule.

However, degrader discovery and optimization remain a slow empirical process. To quantitatively monitor protein-protein complex formation between an E3 ligase, a target protein to be tagged for degradation, and a degrader molecule, several assay formats have been developed. However, all the available assays have certain limitations. For example, some of the assays require recombinant proteins with artificial fluorescent tags to generate a signal and require high protein concentration, which does not reflect the true endogenous protein level in the cell or does not measure the true thermodynamic binding affinity. In addition, many of the assays are not high-throughput.

SPECIFIC PATENTS

U.S. Pat. No. 7,897,381 entitled "Uncoupling of DNA insert propagation and expression of protein for phage display" and owned by the present assignee, provides a vector comprising a modified T7 phage genome.

U.S. Pat. No. 7,112,435 entitled "Uncoupling of DNA insert propagation and expression of protein for phage display" and owned by the present assignee, provides an expression system comprising a modified T7 phage genome.

U.S. Pat. No. 7,833,741 entitled "Uncoupling of DNA insert propagation and expression of protein for phage display" and owned by the present assignee, provides preparation of a heterologous polypeptide comprising a modified T7 phage genome.

SUMMARY

The following is a summary of the invention to provide a basic understanding of some aspects of the invention. This summary is not intended to identify key/critical elements of the invention or delineate the invention's scope. Its sole purpose is to present some concepts of the invention in a simplified form as a prelude to the more detailed description that is presented later.

In various embodiments, provided herein is a method of screening a test compound that binds a target protein of interest and another ligand protein comprising, (i) in the presence and absence of the test compound, incubating an immobilized ligand protein with a target protein of interest, comprising a nucleic acid tag or a detectable tag, wherein the protein of interest and the nucleic acid tag is not the same, (ii) removing any unbound protein of interest and (iii) detecting the presence or absence of a complex between the immobilized ligand protein, test compound and the target protein of interest, wherein an increase in the amount of target protein of interest bound to the immobilized ligand protein in the presence of test compound as compared to the absence of test compound indicates the test compound binds to and promotes protein-protein complex formation between the immobilized ligand protein and the target protein of interest. In various other embodiments, the target protein of interest does not directly bind the immobilized ligand protein but forms a protein-protein complex with the test compound, and the test compound binds the immobilized ligand protein.

In many embodiments, provided herein is a method of screening a test compound that binds a target protein of interest and a ligand protein, wherein the target protein of interest is not previously known to bind to the ligand protein, comprising, (i) in the presence and absence of a test compound, incubating an immobilized protein with a target protein of interest, comprising a detectable tag, wherein the protein of interest and the detectable tag differ from each other, (ii) removing any unbound protein of interest and (iii) detecting the presence or absence of complex formation between the immobilized protein, test compound and the target protein of interest, wherein an increase in the amount of target protein of interest bound to the immobilized protein in the presence of test compound as compared to the absence of test compound indicates the test compound promotes protein-protein complex formation between the immobilized protein and the target protein of interest.

In various embodiments, provided herein is a method of identifying a test compound as molecular glue, wherein the test compound stabilizes the interaction between two proteins that do not normally interact, or that are not previously known to form a complex, said method comprising the steps of: (a) contacting a cell or cell lysate comprising a fusion protein with a test compound, wherein the fusion protein comprises a target protein of interest and a nucleic acid oligomer tag; (b) incubating the fusion protein with the test compound in the presence of an immobilized ligand protein, wherein the ligand protein is immobilized on a solid support; (c) removing any unbound fusion protein; and (d) detecting an amount of fusion protein that binds to the immobilized ligand protein by detecting the nucleic acid oligomer tag bound to the fusion protein; wherein an increase or decrease in the amount of fusion protein of step (d) detected in the presence of said test compound relative to the amount of fusion protein detected in the absence of said test compound indicates that the test compound modulates the interaction between two proteins that do not normally interact.

In various embodiments, an increase in the amount of fusion protein of step (d) detected in the presence of said test compound relative to the amount of fusion protein detected in the absence of said test compound indicates that the test compound promotes protein-protein interaction and complex formation. In various other embodiments, a decrease in the amount of fusion protein bound to the ligand protein of step (d) detected in the presence of said test compound relative to the amount of fusion protein detected in the absence of said test compound indicates that the test compound does not promote protein-protein interaction.

In many embodiments, the immobilized protein can be a ligand protein such as a ligase. In many other embodiments, the immobilized ligand protein can be an E3 ubiquitin ligase.

In various embodiments, the test compound may be a molecular glue compound degrader. In various other embodiments, the test compound is a proteolysis targeting chimeras compound degrader.

In many embodiments, the target protein of interest is individually over expressed in a mammalian cell and exposed to both the test compound and the immobilized ligand protein. The target protein of interest is individually displayed on a phage coat and exposed to both the test compound and the immobilized ligand protein.

In various embodiments, provided herein is a method of identifying a test compound as molecular glue, wherein the molecular glue enables a protein-protein complex between a target protein of interest and a ligand protein that are not previously known to bind, the method comprising (i) incubating a target protein of interest fused to a nucleic acid sequence or a nucleic acid tag with immobilized protein ligand in the presence and in the absence of a test compound, (ii) removing any unbound target protein, and (iii) detecting or quantifying the binding of a target protein of interest to the immobilized ligand protein by quantitative polymerase chain reaction (PCR) or qPCR, wherein an increase in the amount of target protein of interest bound to the immobilized ligand protein in the presence of the test compound as compared to the absence of the test compound indicates that said test compound enables the formation of a protein-protein complex between the target protein of interest and the ligand protein. In many embodiments, the target protein of interest does not directly bind with the immobilized ligand protein but forms a protein-protein complex with the test compound, and the test compound is bound to the immobilized ligand protein.

In various embodiments, provided herein is a method of identifying a test compound as a molecular glue compound degrader, wherein the molecular glue compound degrader promotes a protein-protein complex between a target protein of interest and a ligase that are not previously known to bind, the method comprising (i) incubating a target protein of interest fused to a nucleic acid oligomer with immobilized ligase in the presence and absence of the test compound, (ii) removing any unbound target protein of interest, and (iii) detecting or quantifying the binding of the target protein of interest to the immobilized ligase by quantitative polymerase chain reaction (PCR) or qPCR, wherein an increase in the amount of target protein of interest bound to the immobilized ligase in the presence of the test compound as compared to the absence of the test compound indicates that said test compound enables the formation of a protein-protein complex between the target protein of interest and the ligase and induce ligase dependent degradation. In many embodiments, the target protein of interest does not directly bind the immobilized ligase but forms a protein-protein complex with the test compound, and the test compound binds the immobilized ligase.

In various embodiments, the detectable tag may be a nucleic acid oligomer, wherein the oligomer is bound to the detectable protein, and the oligomer may be radiolabeled, fluorescently labeled, or biotinylated. In some embodiments, the methods provided herein comprise qPCR amplifying the nucleic acid oligomer bound to the target protein of interest.

In many embodiments, a nucleic acid tag on a target protein of interest is employed in a screening assay to identify a test compound as potential molecular glue from a library of compounds, wherein the test compound promotes protein-protein complex formation between the immobilized ligand protein and a target protein of interest. Thus, the disclosed method can be used to screen compounds or candidate compounds via a high throughput assay wherein large libraries of compounds can be screened against the immobilized ligand protein and a target protein of interest and screen compounds capable of forming a protein-protein complex between an immobilized ligand protein and a target protein of interest not previously known to bind.

In many embodiments, the immobilized ligand protein may be a ligase such as E3 ligase. The E3 ligase or E3 ubiquitin ligase tags the target protein or protein of interest for degradation. The disclosed screening assay identifies test compounds that may be used as molecular glue compound degraders and enables protein-protein complex formation between an E3 ligase or E3 ubiquitin ligase and a target protein interest that will be ubiquitinated by the E3 ligase and routed for degradation.

In some embodiments, the present invention discloses a method of screening a test compound for its binding affinities to a protein-protein complex. The method comprises incubating the test compound with one or more proteins of interest and a ligand protein, wherein the ligand protein is immobilized on a solid surface and evaluating the binding properties between the immobilized ligand protein, the protein interest, and the test compound.

In certain embodiments, the disclosure provides a method of screening libraries of compounds against multiple proteins of interest. By this method, the screening assay aid in screening a group of proteins of interest with the test compound wherein once the test compound forms a protein-protein complex between a protein of interest and the immobilized ligand protein, the protein of interest and the test compound can be further evaluated individually.

In many embodiments, the target protein of interest is individually overexpressed in mammalian cells or displayed on a phage coat and exposed to both a test compound and an immobilized ligand protein.

In various embodiments of the methods provided herein, the immobilized ligand protein is immobilized on a solid support. In various other embodiments, the ligand protein is immobilized on a multiwell plate, or the immobilized ligand protein is attached to a solid support bead. The immobilized ligand protein may optionally be labelled with a tag such as, but not limited to, a DNA tag, a fluorescent tag, or a spectroscopic tag.

The assay can be used to identify a molecular glue compound degrader for a protein of interest not previously known. The protein of interest can selectively then be targeted for degradation by the proteasome. The screening assay thus helps in identifying drug candidates that can target disease protein of interest for degradation.

In further embodiments, the E3 ligase of choice is immobilized on a solid phase support bead wherein an E3 ligase of choice will be cloned with an Avi tag at its N-terminus followed by purification and labelling with Desthio-Biotin, and then the labelled ligase is immobilized to a magnetic streptavidin bead.

In many embodiments, a ligand such as protein is immobilized on a solid phase support bead wherein the protein will be cloned with an Avi tag at its N-terminus followed by purification and labelling with Desthio-Biotin, and the labelled protein is immobilized to a magnetic streptavidin bead.

In many other embodiments, the target protein of interest is tagged with a DNA sequence wherein the target protein is cloned within a mammalian or T7 phage gateway vector such as NFkB Gateway vector and expressed in mammalian cells using T7 phage display.

In many embodiments, the target protein of interest is tagged with a DNA sequence to form a fusion target protein, wherein the fusion target protein is expressed in a mammalian cell or within the T7 phage display system.

In many embodiments, the present disclosure related to a molecular glue screening method, comprising immobilizing a ligand protein of choice on a solid support bead, tagging a nucleic acid tag to a target protein of interest to form a fusion protein, incubating the fusion target protein with the immobilized ligand protein in the presence and absence of a test compound, washing the unbound fusion protein and test compounds, and detecting the DNA tag through an ultrasensitive qPCR readout to measure the amount of target protein captured by the ligand protein on the solid support bead in the presence or absence of the test compound. In many embodiments, the ultrasensitive qPCR readout is of the DNA tag on the fusion protein.

In further embodiments, the disclosed assay can screen compounds for properties both as proteolysis targeting chimeras' compounds and molecular glue compounds.

The present invention also provides methods of quantifying the interaction between immobilized ligand protein, such as E3 ligase and test molecules. Also are included business methods for the pharmaceutical development of test molecules evaluated using the techniques described herein. Other aspects include the test molecules, pharmaceutical formulations, and therapeutic and/or prophylactic uses.

Kits for performing the assays described herein are also provided. The kits typically comprise the immobilized ligan proteins and fusion protein comprising target protein of interest and detectable tag and instructions for performing the methods described herein.

These and other features, aspects, and advantages of the present assays and methods will become better understood with references to the following figures and descriptions. This summary is an introduction to the concepts. Additional aspects and advantages of this invention will be apparent from the following detailed description of preferred embodiments, which proceeds with reference to the accompanying drawings.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to illustrate further embodiments of concepts that include the claimed disclosure, and explain various advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
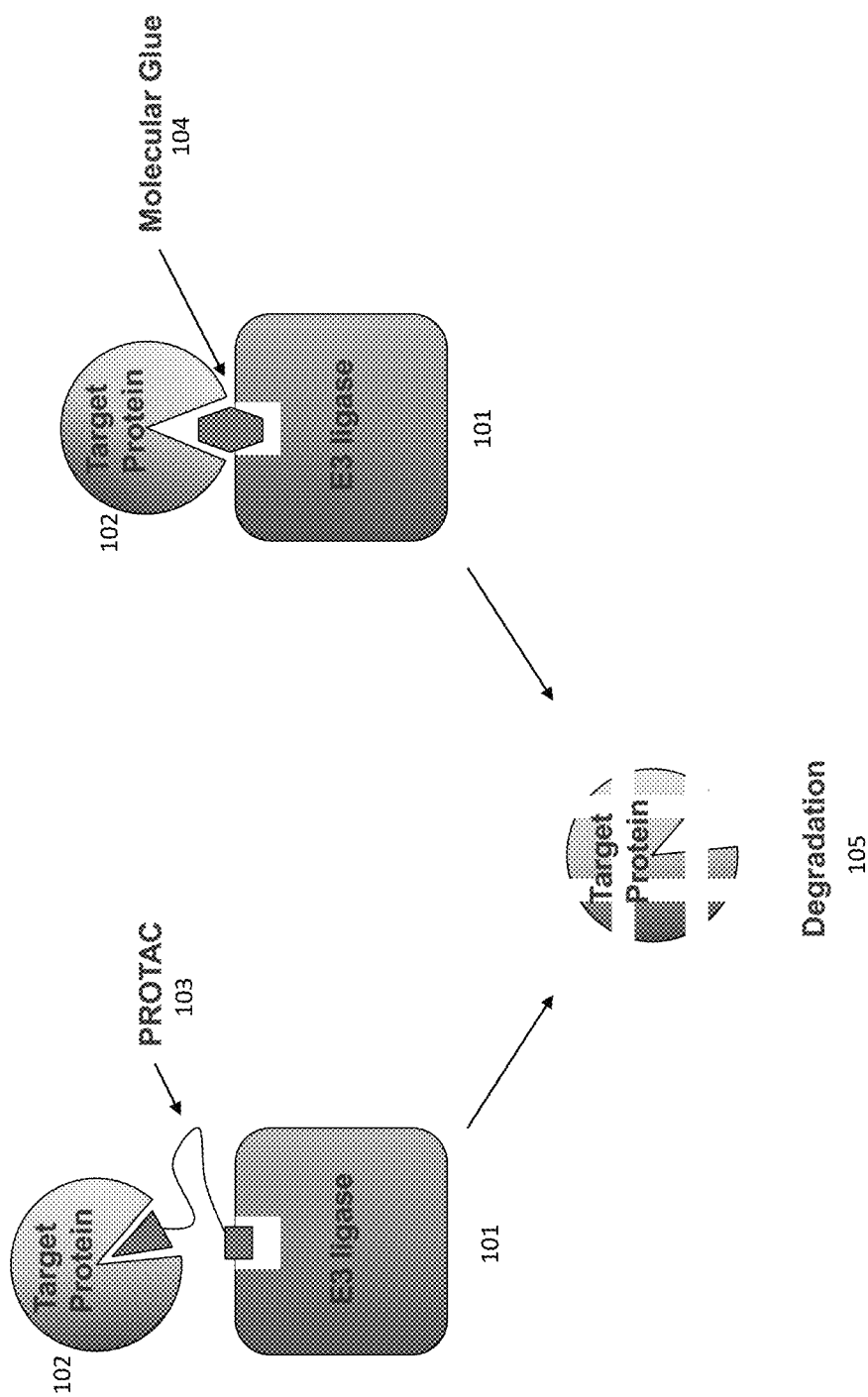
FIG. 1 illustrates a comparison between the proteolysis targeting chimeric technique and the disclosed molecular glue assay.

While the presently disclosed assays and methods are susceptible of embodiment in many different forms, there is shown in the drawings and will herein be described in detail several specific embodiments with the understanding that the present disclosure is to be considered as an exemplification of the principles of the presently disclosed assays and methods and is not intended to limit the disclosure assays and methods to the embodiments illustrated.

Unless defined otherwise, all technical and scientific terms used herein have the same meaning as commonly understood to one of ordinary skill in the art to which this invention belongs.

"Molecular glue" refers to a small molecule or a small compound or a molecule that stabilizes the interaction between two proteins that do not normally interact.

"Compound" or "test compound" or "test molecule" refers to one or more chemical entities such as, but not limited to, a protein, organic or inorganic chemical molecule, synthetic nucleic acids, natural nucleic acids, synthetic polypeptides, natural polypeptides, peptide fragments, proteins, carbohydrate, or other compound, pharmaceuticals and candidate pharmaceuticals which are natural products or which are prepared synthetically. Non-limiting examples include polyketides, steroids, the compounds found in the U.S. Pharmacopoeia, and the products of combinatorial chemical synthesis. Candidate pharmaceuticals include molecules for which no function is known but which have structural similarity to known compounds with one or more known functions. The terms "compound" or "test compounds" as used herein also includes experimental small molecules, FDA-approved small molecule therapeutics, antibodies developed for antibody-directed therapy and other therapeutic agents.

As used herein, the term "target protein" refers to any protein of interest that might be targeted for degradation. In some embodiments, the target protein participates in a cellular process and has enzymatic or catalytic activity.

As well known, proteolysis targeting chimeras (such as PROTAC® s), also known as protein degraders, are small molecules composed of two ligand domains such as a domain to bind a protein of interest and a domain to bind E3 ubiquitin ligase wherein the two ligand domains are linked via a linker resulting in a small molecule capable of bringing to close proximity the E3 ligase and the protein of interest, enabling tagging of the protein of interest for degradation and removing it through the cellular proteasomal degradation system. However, the approach has certain flaws and challenges due to the size of the PROTAC® molecule, the unwanted flexibility of the linker, and the inability of PROTAC® to enable the degradation of certain proteins of interest.

The disclosed assays and methods overcome the challenges by providing a screening assay such as a molecular glue screening assay wherein a test compound is screened to act as a glue or a molecular glue between a protein of interest and an E3 ligase. In addition, such molecular glue screening assays can be utilized to screen for proteolysis targeting chimeras molecules using the same principle.

The disclosed assay can screen compounds for both proteolysis targeting chimeras and molecular glue compounds. In many embodiments, using a library of compounds comprising natural compounds or non-synthetic compounds, the assay may help screen molecular glue compounds, whereas using a library of synthetic compounds will help potential screen proteolysis targeting chimeras molecules.

As shown in FIG. 1, the currently available technology use PROTAC® (103) as a molecule having two ligand binding sites wherein the PROTAC® (103) binds a target protein (102) at one end and E3 ligase (101) on the other end. The E3 ligase (101) target the protein of interest (102) for degradation (105), routing the protein to proteosome. However, the technology suffers from various disadvantages. The relatively large-size of PROTAC® molecules can severely affect their binding properties. Further, the technology suffers from its inability to bind all proteins because of the lack of complex formation between a protein of interest and E3 ligase, and the chemical synthesis of even small molecule PROTAC® s is much difficult.

The disclosed screening assay aid in screening compounds, which may function as molecular glue or proteolysis targeting chimeras between a target protein and an E3 ligase protein such that the E3 ligase can tag the target protein of interest for protein degradation. The target protein may or may not be degraded; however, the test compound can be used to form a complex between the protein of interest and a protein ligand of choice such as E3 ligase to aid in tagging the protein of interest for degradation.

As further shown in FIG. 1, a molecular glue (104) compound can act as a binding agent forming a complex between the target protein (102) and E3 ligase (101). The E3 ligase (101) and target protein form a complex wherein both the target protein and E3 ligase bind to the test compound or molecular glue (104). The binding of E3 ligase with the target protein of interest tags the protein for degradation (105) and thus routing the protein for degradation.

Among many advantages of the disclosed assays and methods, the absence of linker and small size compounds functioning as molecular glue provide better therapeutic targets for degraders in TPD.

A molecular glue binds together structures at the molecular level by changing the surface of the target molecule, allowing it to attach to another protein. Thus, the present disclosure provides an assay for screening a test compound for its function as a molecular glue and promoting protein-protein complex formation between two proteins that are previously not known to bind each other.

A fusion protein may comprise of a protein of interest and a nucleic acid tag such as a DNA tag or a nucleic acid oligomer. In some embodiments, the methods provided herein comprise qPCR amplifying the nucleic acid oligomer that is bound to the protein of interest. In some embodiments, the nucleic acid oligomer is radiolabeled, fluorescently labeled or biotinylated.

In many embodiments, a nucleic acid tag is employed in a screening assay to identify from a large number of test compounds capable of forming a complex between the immobilized ligand protein and target protein of interest. Thus, the disclosed method can be used to screen candidate compounds via a high throughput assay wherein large libraries of compounds can be screened against a protein of interest and immobilized ligand protein of choice.

Figure 2:
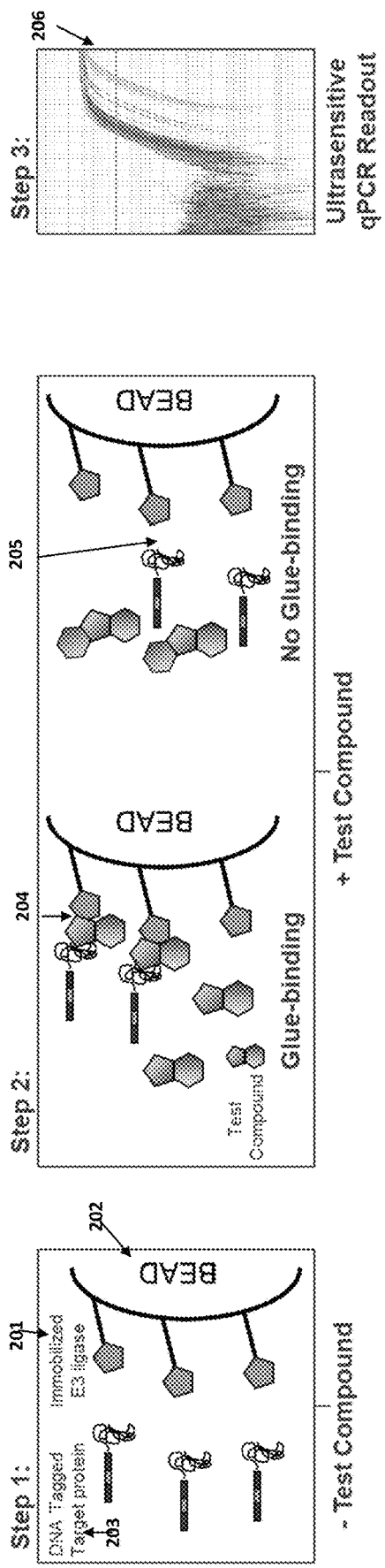
FIG. 2 illustrates the disclosed screening assay principle.

FIG. 2 shows the principle of the disclosed screening assay wherein E3 ligase is immobilized (Step 1, 201) on a bead surface (202) such as a magnetic streptavidin bead surface, and a target protein is tagged with a DNA sequence (203) for its quantification via qPCR or other such techniques. The immobilized E3 ligase and the DNA tagged target protein is further incubated with a test compound, wherein if a test compound binds with the immobilized E3 ligase and target protein to form a complex (Step 2, 204) such that the test compound is functioning as a molecular glue between the target of interest and the immobilized E3 ligase a higher signal will be generated (Step 3, 206). Further, if the test compound does not initiate or form a complex between the target protein and immobilized E3 ligase (205), a lower signal will be detected in the qPCR stage, showing that the test compound is not acting as a molecular glue between the target protein and immobilized E3 ligase of choice. The E3 ligase is not limited to a specific domain to be able to bind the test compound functioning as a molecular glue.

The DNA sequence tag will be quantified using the quantifiable PCR or qPCR, and an ultrasensitive readout will be displayed on a screen (206).

A great variety of vectors can be used to practice the methods as disclosed herein. Such vectors include, but are not limited to, vectors derived from bacterial plasmids, from bacteriophage, from yeast episomes, from yeast chromosomal elements, from mammalian viruses, from mammalian chromosomes, and vectors derived from combinations thereof, such as those derived from plasmid and bacteriophage genetic elements, such as cosmids and phagemids. Generally, any vector suitable to maintain, propagate or express polynucleotides in a cell may be used. Examples of bacteriophage vectors that are capable of self-propagation and protein display include, for example, Novagen's 10-3 T7 and 1-1 T7 strains.

The selection of appropriate vectors, including phage-based vectors, for propagation or transfer of nucleic acids is well known in the art. The requisite techniques for vector construction, the introduction of the vector into the host, and propagation or expression in the host are routine to those skilled in the art.

The following vectors, which are also commercially available, are provided by way of non-limiting examples as an alternative to vectors that are derived from phage genomes. Among vectors for use in bacteria pQE70, pQE60, and pQE-9, available from Qiagen; Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. These vectors are listed solely by way of illustration of the many commercially available and well-known vectors that are available to those of skill in the art for use in accordance with the present invention. It will be appreciated that any other plasmid or vector suitable for, for example, introduction, maintenance, propagation, and/or expression of a polynucleotide or polypeptide of the invention in a host may be used in this aspect of the invention.

In the disclosed screening assay, the partner target protein of choice is tagged with a DNA sequence wherein the target protein is cloned within a mammalian or T7 phage gateway vector such as NFkB Gateway vector and expressed in mammalian cells or using T7 phage display.

A variety of different phage derived constructs may be used in the practice of the disclosed methods. In preferred embodiments of the disclosed methods, the constructs are phage genomes that have been modified to be capable of conditionally expressing a heterologous polypeptide as a fusion protein with protein of interest, as discussed herein. The modified phage genomes preferably retain the regulatory and coding sequences found therein. Preferred phage genomes for the practice of the invention are those of lytic phages, not limited to T7, T4, T3 and lambda phage, and filamentous phages.

In other embodiments, the ability to express a fusion protein comprising a target protein of interest with a nucleic acid oligomer is regulated in part by the use of a regulated promoter or another regulatory region (e.g. an inducible promoter such that in the absence of induction, expression controlled by them is low or undetectable). Non-limiting examples of inducible promoters include the lac promoter, the lac UV5 promoter, the arabinose promoter, and the tet promoter.

A "modified T7 phage genome" refers to a T7 genome, which comprises nucleotide sequence changes or deletions relative to the wild type genome (GenBank Accession No.: V01146.1). A modified T7 phage genome comprises a complete or partial deletion of nucleotide sequence(s) encoding one or more or all of the T7 nonessential genes. Complete or partial deletion preferably results in the inactivation of the given gene. A nonessential gene is a gene that can be fully or partially deleted from the phage genome without affecting its viability. Nonessential genes are those genes that are not essential to the T7 phage life cycle.

As further provided in the disclosed methods, a ligand protein is preferably immobilized on a solid support. Immobilization of the ligand protein on solid support may be by a variety of means or standard means of covalently or non-covalently coupling a molecule to solid supports are well known in the art. Non limiting examples include the use of linker molecules, crosslinkers such as glutaraldehyde, and biotin/avidin interactions. An example of the latter is with the use of biotin covalently coupled to a molecule and avidin bound to a solid support. The solid support itself can take any convenient form, typically a culture dish or plate or bottle, a well of a multi-well culture dish or plate, a bead, a column containing particles to which a molecule is immobilized, or a planar surface containing the immobilized molecule. Other non-limiting examples of a solid support include agarose, polystyrene or other polyvinyl compounds, and magnetic beads.

As provided in the disclosed methods, a biotin-streptavidin interaction is used to immobilize a ligand protein on magnetic beads. The ligand protein is covalently linked to biotin (directly or via a linker), which is bound to streptavidin coated magnetic beads. After contact with the member(s) of a group or family of polypeptides and a test molecule, the beads are isolated and the ligand proteins are eluted. A variety of elution conditions may be used. Non-limiting examples include elution with a soluble version of the ligand protein that lacks biotin; elution with a detergent solution, such as one containing SDS, which denatures the polypeptide(s) to disrupt binding to the ligand protein; and elution with a protease containing solution to cleave the ligand protein from the phage. The first elution example is preferred to elute bound ligand protein based on binding to the test molecule and protein of interest. In alternative embodiments of the invention, other versions of streptavidin, such as monomeric avidin with a lower affinity for biotin, are used such that elution with free biotin may be used. The eluted protein may be quantified by any appropriate means, including, but not limited to, standard phage tittering methods, such as a plaque forming assay or by quantitative PCR (qPCR).

While the above discussion details particularly mild elution conditions, which may be advantageous under some conditions, it is not a necessary feature of the invention. Covalent bonding of a ligand protein to a solid support is also practical, and elution can be affected by methods appropriate to this system.

Aspects of the methods include the use of a vector comprising a modified T7 phage genome, which is extensively described in the aforementioned reference U.S. Pat. No. 7,897,381 issued on Mar. 1, 2011, whose method section is specifically incorporated by reference as if set forth in its entirety herein.

Aspects of the method include the use of an expression system comprising a modified T7 phage genome, which is extensively described in the aforementioned reference U.S. Pat. No. 7,112,435 issued on Sep. 26, 2006, whose method section is specifically incorporated by reference as if set forth in its entirety herein.

Aspects of the method include preparation of a heterologous polypeptide comprising a modified T7 phage genome, which is extensively described in the aforementioned reference U.S. Pat. No. 7,833,741 issued on Sep. 26, 2006, whose method section is specifically incorporated by reference as if set forth in its entirety herein.

Any of the methods described herein can be run in either singleplex or multiplex format. In one exemplary multiplex format, a test compound is screened and tested for its binding properties against multiple proteins of interest from a panel of such proteins simultaneously. Where multiple proteins are being assayed simultaneously or sequentially, nucleic acid oligomers or a detection tag unique to a protein of interest can be used to distinguish the activity of each protein of interest.

In many embodiments, the disclosed screening assay provides a protein-protein complex formation assay where two proteins form a complex in the presence of a molecular glue compound. Further, the assay can help identify a partner protein for a protein of interest. The screening assay also helps in forming protein-protein complex, wherein a protein forms a complex with E3 ligase, and thus the ligase can tag the protein of interest for degradation, though the protein may or may not be degraded.

The ligand protein may be coupled covalently to the solid support bead or maybe noncovalently bound by a system that permits the release of the entire complex containing a bound target protein of interest and the ligand protein.

As provided herein, the target protein of interest may be a substrate for a kinase, transferase, oxidoreductase, hydrolase, ligase, isomerase or lyase. Further, the target protein of interest may be a human polypeptide or protein. The target protein of interest may be modified by cleavage, by the addition or removal of functional groups or by undergoing isomerization. In certain embodiments, the target protein of interest may be a substrate of a transferase having transferase activities, such as an acyltransferase, glycosyltransferase, amidotransferase or sulfurtransferase. Additionally, the target protein of interest may be a G-coupled protein receptor, an ion channel protein, a nuclear receptor protein, a transcription factor, a kinase, a cytokine, a growth factor, a hormone, an enzyme, a kinase, a substrate for a protein kinase, a substrate for lipid kinase, a substrate for a tyrosine kinase, a receptor, a substrate for a serine/threonine kinase, a substrate for a human non-receptor tyrosine kinase, a substrate for a human receptor tyrosine kinase, an antibody or a small chain variable fragment (scFv) a substrate for a hydrolase, peptidase, protease or phosphatase or an enzyme or a kinase modified by autophosphorylation.

In certain embodiments, a nucleic acid encoding the target protein of interest is cloned into a plasmid expression vector and transiently transfected into a cell line, resulting in transient expression of the target protein of interest. In certain embodiment, a nucleic acid encoding the target protein of interest is cloned into a plasmid expression vector and stably transfected into a cell line, resulting in stable expression of the target protein of interest. In certain embodiments, a nucleic acid encoding the target protein of interest is cloned into a constitutive plasmid expression vector and transfected into a cell line, resulting in constitutive expression of the target protein of interest. In specific embodiments, constitutive expression is under the control of a CMV promoter. In certain embodiments, the nucleic acid encoding the target protein of interest is cloned into an inducible plasmid expression vector and transfected into a cell line, resulting in the inducible expression of the target protein of interest. In specific embodiments, inducible expression is under the control of a CMV promoter containing operator sites. In a more specific embodiment, the operator sites are tetracycline operator 2 sites. In yet another embodiment, the inducible plasmid expression vector is a tetracycline-regulated expression vector.

Techniques for the construction of expression vectors and expression of genes in cells comprising the expression vectors are well known in the art. See, e.g., Sambrook et al., 2001, Molecular Cloning—A Laboratory Manual, $3^{rd}$ edition, Cold Spring Harbor Laboratory, Cold Spring Harbor, N.Y., and Ausubel et al., eds., Current Edition, Current Protocols in Molecular Biology, Greene Publishing Associates and Wiley Interscience, NY.

As further provided in the disclosed methods, the nucleic acid sequence of the nucleic acid tag comprises an amplicon linked to a target DNA sequence specifically recognizable by a DNA-binding protein (e.g., NFκB, cro repressor, GAL4, GCN4, LexA, Opaque-2 and TGA1a) and is capable of binding or otherwise linking to a protein of interest having a DNA-binding component. The nucleic acid tag may then be detected and/or quantified using, e.g., quantitative PCR (qPCR) or the nucleic acid tag may be PCR-amplified and detected by mass spectrometry.

In some embodiments, a second reporter function is employed during the PCR amplification step. In one specific embodiment, during the PCR amplification step, the nucleic acid tag undergoes a primer extension step, at which time a second reporter function such as a fluorescent tag becomes attached to the nucleic acid tag.

The nucleic-acid tag may be detected and/or quantified by qPCR. Nucleic acid tag detection by qPCR has the advantage of being not only a reliable quantitative detection method but also a highly sensitive and highly selective detection method. Because of the highly sensitive nature of the qPCR detection method, this method enables the detection of very small amounts of the target protein and reduces the need for scarce and expensive assay components, such as recombinant proteins. Because of the highly specific nature of the qPCR detection method, qPCR also enables the detection of specific DNA sequences in complex heterogeneous mixtures and obviates the need for any sort of purification steps normally done to protein samples to either improve or enhance protein detection.

The amplifiable sequence hybridizes or is capable of hybridizing to a PCR primer in a sequence-specific manner.

In certain embodiments, the nucleic acid tag comprises a plurality of amplicons, for example, two, three, four, five, six, seven, eight, nine, ten or more amplicons. In some embodiments, the plurality of amplicons is tandem repeats of a single amplicon. In certain embodiments, the amplicon is amplifiable by quantitative PCR, which permits quantification of the protein tagged by such a nucleic acid oligomer. In a specific amplification method, amplification of a PCR sequence includes combining the nucleic acid containing the PCR amplification template, PCR primer and qPCR probe in a standard PCR reaction mixture (generally, a mixture having a final concentration of 10 mM Tris-HCl (pH 8.3 at 25° C.), 1-4 mM $MgCl_2$, 0.1-1 mM dNTP), and treating the sample first under Hot Start conditions (for example, heating to 95° C. for 5 minutes) to minimize nonspecific annealing or mispriming, followed by a denaturation step (for example, 95° C. for 45 seconds), followed by an annealing step (55° C. for 1 minute), and followed by an extension step (72° C. for 1 minute), with up to forty rounds of the consecutive steps of denaturation, annealing and extension, to complete the amplification of the qPCR signal.

In one embodiment, the length of the nucleic acid tag is between about 50 and about 100, about 50 and about 200, about 50 and about 300, about 50 and about 400, about 50 and about 500, about 100 and about 200, about 100 and about 300, about 100 and about 400, about 100 and about 500, about 200 and about 300, about 200 and about 400, about 200 and about 500, about 300 and about 400, about 300 and about 500, or about 400 and about 500 nucleotides in length.

The reporter function of the nucleic acid tag may also come from the radiolabeling, fluorescent labeling or biotinylation of the nucleic acid tag. The nucleic acid tag may be single- or double-stranded DNA, single- or double-stranded RNA, DNA-RNA hybrid, RNA-RNA hybrid, or their native or synthetic derivatives, analogs and fragments thereof. In some embodiments, the nucleic acid tag is DNA, and the reporter function label can be introduced to the DNA, for example, by any standard enzymatic reaction, such as nick translation, or by terminal labeling, with $^{32}P$, $^{125}I$ or biotin-labeled deoxynucleotide triphosphates (dNTPs), or the label can be introduced as an intercalating agent. There are many fluorescent or luminescent groups that are commercially available and can be used to label the nucleic acid tag. Some examples of fluorescent labels that can be used to label the nucleic acid tag are fluorescein, rhodamine and coumarin and their commercial derivatives such as Texas Red® and Alexa Fluor®. Examples of luminescent groups are lanthanide complexes and luminescent nanoparticles. In one embodiment, the nucleic acid tag does not initially have a reporter function, but a reporter function is added before the nucleic acid detection step.

The disclosed assay may be carried in cells which may be primary cells, secondary cells or immortalized cells of any cell type and origin. In some embodiments, cells are of mammalian origin, including humans. In some embodiments, cells are of different cell types. In other embodiments, cells are from a substantially homogeneous population of cells. The methods of the invention allow an analysis of large numbers of cell samples contained, for example, in 42-, 96-, 384-, or 1536-well assay plates.

The methods provided herein may be carried out using any cell types that can be grown in standard tissue culture plasticware. Such cell types include all normal and transformed cells derived from any recognized sources, for example, mammalian, plant, bacterial, viral or fungal. In particular embodiments, cells are of mammalian (human or animal, such as rodent or simian) origin. In some embodiments, the cells are of human origin. In some embodiments, the cells are of rodent origin. In some embodiments, the cells are of murine origin. In some embodiments, mammalian cells may be of any organ or tissue origin (e.g., brain, liver, lung, heart, kidney, skin, muscle, bone, bone marrow or blood) and of any cell type. Suitable cell types for use in the methods provided herein include, but are not limited to, fibroblasts, basal cells, epithelial cells, endothelial cells, platelets, lymphocytes, T-cells, B-cells, natural killer cells, reticulocytes, granulocytes, monocytes, mast cells, neurocytes, neuroblasts, cytomegalic cells, dendritic cells, macrophages, blastomeres, endothelial cells, tumor cells, interstitial cells, Kupffer cells, Langerhans cells, littoral cells, tissue cells such as muscle cells and adipose cells, enucleated cells, and the like.

In some embodiments of the methods described herein, the cells may be genetically engineered to express the fusion protein comprising the target protein of interest and the nucleic acid oligomer or a nucleic acid tag. Expression vectors can be introduced into the host cell for expression by any method known to one of skill in the art without limitation. Such methods include, but are not limited to, e.g., direct uptake of the molecule by a cell from solution; or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, an RSV promoter, a tetracycline-inducible CMV promoter (such as the human immediate-early CMV promoter), and a constitutive CMV promoter. The expression vectors should contain expression and replication signals compatible with the cell in which the fusion protein is to be expressed. Expression vectors useful for expressing the target protein of interest or fusion protein described herein include viral vectors such as retroviruses, adenoviruses and adeno associated viruses, plasmid vectors, cosmids, and the like.

Any mammalian cell known by one of skill in the art to be useful for expressing a recombinant polypeptide, for example, Chinese hamster ovary (CHO) cells, HeLa cells, A375 cells, HEK293 or LnCap cells, can be used to express the fusion protein comprising the target protein of interest and the detection tag, such as a nucleic acid tag. When the target protein is expressed in the appropriate host cell, it can exhibit post-translational modification that is present in native protein and is therefore expected to have the structure and function of a native protein.

In another aspect, the invention provides a method of screening libraries of compounds against one or more polypeptides. Typically, groups of test molecules are tested with the polypeptide of interest, and once a binding interaction of interest has been identified, the test molecules can be further evaluated individually.

In another aspect of the invention, libraries of compounds are screened for their binding properties to individual polypeptides or to sets of polypeptides. Multiple compounds may be tested at one time. Typically, if multiple compounds are tested, following a positive interaction, the compounds are individually evaluated for their binding properties.

Also provided herein is a kit for screening a candidate molecule or a test compound as molecular glue, wherein the test compound enables a protein-protein complex between a target protein of interest and a ligand protein that are previously not known to bind each other. Such a kit may comprise a cell line transfected with the fusion protein comprising a target protein of interest and a detectable tag that serves as the detectable substrate in the cellular assay. Such a kit may further comprise a ligand protein that forms a complex with a target protein that forms a complex with the test compound. The ligand protein is immobilized onto solid support or a container, such as a well in a multiwell plate. In some embodiments, the kit further comprises a detectable nucleic acid tag; and a target protein capable of being "tagged" by the nucleic acid tag. Where the nucleic acid tag is detectable by qPCR, the kit may additionally include a PCR primer capable of recognizing a PCR initiation sequence in the nucleic acid tag. Such a kit may be used to carry out the methods of identifying test compounds capable of forming a protein-protein complex between two proteins that is otherwise not known to bind each other, as described above.

The disclosed assays and methods further provide advantages as compared to the use of small molecule drugs to target a disease protein of interest. Among many advantages, molecular glue can target or bind to undruggable targets, transcription factors, translation factors, scaffold proteins, enzymatic proteins, and non-enzymatic proteins. The molecular glue compound can bind to a non-functional domain of the target protein and E3 ligase and not only at the active site. The disclosed assays also provide the ability to develop molecular glue degrader drugs with tissue selectivity and sub-stoichiometric potency, which is otherwise difficult to achieve using small molecule inhibitor drugs.

In the description, for purposes of explanation and not limitation, specific details are set forth, such as particular embodiments, systems, methods, etc. in order to provide a thorough understanding of the present technology. However, it will be apparent to one skilled in the art that the present technology may be practiced in other embodiments that depart from these specific details.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While specific embodiments of, and examples for, the method is described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel or may be performed at different times.

While various embodiments have been described above, it should be understood that they have been presented by way of example only and not limitation. The descriptions are not intended to limit the scope of the present technology to the particular forms set forth herein. On the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A method of identifying a test compound as molecular glue, wherein the test compound stabilizes interaction between two proteins not previously known to interact, said method comprising the steps of:
   (a) contacting a cell or cell lysate comprising a fusion protein with the test compound, wherein the fusion protein comprises a target protein of interest and a nucleic acid oligomer tag;
   (b) incubating the fusion protein with the test compound in the presence of an immobilized ligand protein, wherein the ligand protein is immobilized on a solid support;
   (c) removing any unbound target protein of interest from the cell or cell lysate; and
   (d) detecting an amount of the fusion protein that binds to the immobilized ligand protein by detecting the nucleic acid oligomer tag bound to the fusion protein; wherein an increase in the amount of the fusion protein of step (d) detected in the presence of the said test compound relative to the amount of the fusion protein detected in the absence of the said test compound indicates that the said test compound modulates the interaction between two proteins not previously known to interact.

2. The method of claim 1, wherein an increase in the amount of the fusion protein of step (d) detected in the presence of the said test compound relative to the amount of the fusion protein detected in the absence of the said test compound, indicates that the test compound promotes protein-protein interaction between the two proteins.

3. The method of claim 1, wherein the immobilized ligand protein is a ligase.

4. The method of claim 3, wherein the ligase is E3 ubiquitin ligase.

5. The method of claim 1, wherein the protein ligand is immobilized to a solid support bead.

6. The method of claim 3, wherein the ligase tags the target protein of interest for degradation.

7. The method of claim 1, wherein the test compound is a small molecule.

8. The method of claim 1, wherein the test compound is a protein.

9. The method of claim 1, wherein the test compound is a proteolysis targeting chimeras compound degrader.

10. The method of claim 1, wherein the target protein of interest is individually overexpressed in a mammalian cell and exposed to both the test compound and the immobilized ligand protein simultaneously.

11. The method of claim 1, wherein detecting the amount of the fusion protein is by quantitative PCR.

12. The method of claim 1, wherein the method further comprises contacting an expression vector comprising the fusion protein with the test compound.

13. The method of claim 1, wherein the test compound enables the formation of a protein-protein complex between the target protein of interest and the immobilized ligand protein.

14. The method of claim 1, wherein the test compound binds to the immobilized ligand protein.

15. The method of claim 1, wherein the method identifies the test compound as molecular glue from a library of compounds.

16. The method of claim 13, wherein the method screen the test compound for its binding affinities to the protein-protein complex between the target protein of interest and the immobilized ligand protein.

17. The method of claim 1, wherein the method further comprises
   incubating the test compound with one or more target proteins of interest and the immobilized ligand protein, wherein the ligand protein is immobilized on a solid surface; and
   evaluating the binding properties between the immobilized ligand protein, the protein of interest, and the test compound.

18. The method of claim 1, wherein the immobilized ligand protein is labelled with a tag.

19. The method of claim 1, wherein the target protein of interest is cloned within a mammalian or a T7 phage gateway vector.

* * * * *